United States Patent [19]
Allen et al.

[11] Patent Number: 4,963,668
[45] Date of Patent: Oct. 16, 1990

[54] WELAN GUM IN CEMENT COMPOSITIONS

[75] Inventors: Floyd L. Allen, Escondido; Glen H. Best, San Diego; Thomas A. Lindroth, Spring Valley, all of Calif.

[73] Assignee: Merck & Co., Inc., Rahway, N.J.

[21] Appl. No.: 366,063

[22] Filed: Jun. 14, 1989

Related U.S. Application Data

[63] Continuation of Ser. No. 181,844, Apr. 15, 1988, abandoned, which is a continuation-in-part of Ser. No. 47,748, May 7, 1987, abandoned.

[51] Int. Cl.$^5$ .................... C08B 37/00; C07H 1/00
[52] U.S. Cl. .................... 536/114; 536/124; 435/252.1; 435/829

[58] Field of Search .................... 536/114, 124, 119; 435/252.1, 829

[56] References Cited

U.S. PATENT DOCUMENTS 4,342,866  8/1982  Kang et al. .................... 536/119

*Primary Examiner*—Ronald W. Griffin
*Assistant Examiner*—Everett White
*Attorney, Agent, or Firm*—Curtis C. Panzer; Hesna J. Pfeiffer; Gabriel Lopez

[57] ABSTRACT

Low viscosity welan gum having a 5% (wt.) aqueous solution viscosity of 100 cP and process for preparation of such are described.

2 Claims, No Drawings

WELAN GUM IN CEMENT COMPOSITIONS

CROSS REFERENCE

This is a continuation of application Ser. No. 181,844, filed Apr. 15, 1988, now abandoned, which is a continuation in part of U.S.S.N. 47,748, filed May 7, 1987, now abandoned.

BACKGROUND OF THE INVENTION

Concretes and mortars are cement compositions additionally containing aggregate (e.g., sand and rock) and water. When water is added to the cement, this forms a paste which then hardens to a solid structure. Various additives have been used in these cement compositions to modify their properties for specialized applications. Thus, long fibers such as asbestos reduce the sagging of these pastes and thus is beneficial when applying tiles to a vertical surface. Freezing point depressants are used when cements are to be poured in subfreezing temperatures. Cellulosic polymers have been used in cements to control sedimentation of particles in the pastes. Bentonite clay has been used for this purpose. Other polymers, such as the polyvinyl alcohols and methyl methacrylates, have been used to reduce friction when pumping these pastes and to otherwise modify their workability. Fumed silica is used as an additive to make stronger concrete with reduced permeability.

SUMMARY OF THE INVENTION

It has now been found that cement compositions comprising 0.01 to 0.9% welan gum by weight of dry cement exhibit improved workability, suspension of aggregates, air entrainment, sag resistance, flow characteristics, and resistance to water loss. Furthermore, these improvements are retained at elevated temperatures (i.e., greater than 93° C.). Preferably the range of welan gum is 0.1–0.5%.

DETAILED DESCRIPTION

By cement compositions is meant hydraulic cements, i.e., finely ground and calcined calcium silicates and calcium aluminates which when mixed with water react to form a hard, rock-like mass. By cement, as used herein, therefore, is meant numerous well known cement compositions, such as: portland cement, portland pozzolan cement (containing about 15–40% pozzolan) blast furnace slag cement, slag cement (containing blast furnace slag and hydrated lime), masonry cement (e.g., adhesive mortars), construction concrete (containing sand and aggregate, oil well cement (i.e., cements with retarders to prevent rapid setting so that they may be used at high temperatures and pressure environments of deep wells), aluminous cement (containing high amounts of calcium aluminates, expansive cements (containing high sulfate and alumina concentrations and which expand on hardening), air entrained cement (containing compounds which retain air bubbles and thus yield frost- and chemical resistant concretes), lightweight concrete (containing low density materials such as furnace clinker, pumice, foamed slag, fly ash, gas, wood, etc.) heavy concrete (containing dense material such as barite, iron ore (i.e., illmenite or hematite), steel, etc.), and low heat concrete (with modified compositions that minimize heat generation during the setting process).

With respect to oilfield cements, it is desirable, while drilling a subterranean well, to line the surface of the hole with hollow pipe known as casing. The casing is held in place by attaching the casing to borehole wall with a cement slurry. The cement slurry is put in place by pumping the slurry down the inside of the casing to the bottom of the hole and up the annulus between the casing and borehole wall. The cement is then allowed to set for several hours to gain strength before any other operation are commenced.

The purpose of primary cementing is:
1. To add support for the casing by physical bracing or prevention of formation pressure being imposed on the casing.
2. To allow segregation of individual formations behind the pipe so that fluids from one formation cannot flow into another. This allows production from a specific zone.
3. To retard corrosion by minimizing contact between the casing and corrosion formation waters.

Oilfield cements are basically the same as those used in constructions (i.e., portland cement). The American Petroleum Institute has set specifications for oilfield cements. These as classified as "A" through "H", "J" and "N", all of which are useful in the compositions of this invention.

Cement additives in oilfield cements are materials mixed in the slurry for one or more of the following purposes:
1. Reducing or increasing density;
2. Increasing volume at reduced unit cost;
3. Accelerating or retarding slurry thickening time;
4. Increasing strength;
5. Preventing loss of whole cement slurry;
6. Increasing or improving the durability;
7. Decreasing water loss from the slurry;
8. Increasing or decreasing the viscosity of the cement slurry.

The water loss of a "neat" cement slurry (cement and water only) is very high and rapid. When a slurry contacts a porous formation rock (such as an oil bearing sandstone) it may become quickly dehydrated by the water filtering into the formation. This causes the cement to "flash set." This may cause the casing to stick to the borehole before all the slurry is pumped in the annulus or before the casing is in the proper position.

Bentonite in concentrations of 0–14% (wt./wt. of dry cement) is used to control the water loss from the slurry. Carboxymethylhydroxyethyl cellulose (CM HEC) and hydroxyethyl cellulose (HEC), cellulosic polymers, are used at levels from 0.2 to 0.9%.

It is an object of this invention to use welan gum for controlling water loss from cement slurries at gum concentrations of 0.01–0.9% (wt.), preferably 0.1–0.5%. Welan gum (also known as S-130) is a heteropolysaccharide described in U.S. Pat. No. 4,342,866. Thus, an embodiment of this invention is a process for controlling water loss from cement slurries which comprises incorporating into said slurries 0.01–0.9% (preferably, 0.1–0.5) welan gum, based on dry weight. In a preferred embodiment of this invention, the slurry temperature is in the range 93°–127° C.

Welan gum does not have the effect of lowering the slurry density and increasing the water required as does bentonite. The cellulosic polymers are strong retarders and require dispersants. The cellulosics lose their effectiveness for controlling water loss as the temperature increases and are almost nonfunctional above 93° C. Welan gum does not require a dispersant and shows good funtionality up to 127° C. at a lower concentration than cellulosic polymers.

It is a further object of this invention to use welan gum as a suspending agent for cement slurries. Although welan gum has been described in U.S. Pat. No. 4,342,866 to be an excellent viscosifier and suspending agent in aqueous brines, it was unexpected that the polymer would be compatible with and increase the suspension properties of cement slurries. Many other commercially available polymers are not compatible or functional in cement slurries. The compatibility and suspension properties of welan gum are advantageous in several oilfield and industrial applications. For example, welan gum increases the workability of cement compositions, i.e., it improves the ability of cement slurries to be easily placed in crowded areas such as around reinforcing bars without aggregate settling. Under such conditions a stiff or "dry" concrete slurry would be extremely difficult to position but a more mobile "wet" slurry would produce a weak concrete and would allow settling of aggregate.

Thus, another embodiment of this invention is a process for improving the suspension of cement slurries which comprises incorporating therein 0.01–0.9% (preferably, 0.1–0.5) welan gum, based on dry weight of cement. In a preferred embodiment of this invention the slurry temperature in 93°–127° C.

In these applications the use of an additive or admixture dispersing (or plasticizing) the cement slurry is commonly used. The dispersant lowers the viscosity of the slurry so that handling, pumping, or other positioning of the slurry is made possible. Once the slurry is dispersed and the viscosity lowered, settling of the cement particles begins and separation of the water from the slurry toward the surface is greatly accelerated. The use of welan gum controls separation in these dispersed cement compositions. The concentration of dispersant (or plasticizer) may vary greatly depending on the slurry formulation, additive used, and percent water needed in the application. In general, the dispersant concentration is between 0.1 and 1.5% based on the weight of dry cement in the slurry.

Another embodiment of this invention is a cement slurry comprising 0.1 to 1.5% dispersant and 0.01–0.9% (preferably, 0.1–0.5) welan gum, both based on dry weight of cement.

Cement slurries containing welan gum show more uniform density as the curing process proceeds. The suspension properties of welan gum keeps the slurry more uniform, yielding less aggragate settling and less free water on the surface of the slurry.

Since welan gum is an excellent cement suspension aid, it can be used to suspend liquid mixtures that are subsequently added to cement slurries. For example, fumed silica, a white fluffy powder containing almost 100% amorphous silicon dioxide is a concrete additive used to produce high strength, low permeability concrete. Because of its extremely low bulk density, in the powder form it is very difficult to handle. Therefore, aqueous formulations of fumed silica are desirable and convenient. However, such formulations tend to settle out on standing for a day or more. The suspending properties of welan gum make its use in fumed silica aqueous compositions highly advantageous and such compositions are a convenient way to add welan gum to cement compositions. Similar aqueous compositions are within the scope of this invention utilizing welan gum's ability to suspend particulate materials in cement additives.

In some applications, the cement slurry is viscous enough that additional viscosity imparted by an additive such as welan gum would be undesirable in terms of handling or positioning the slurry. This is particularly true for cements where it is desirable to achieve the lowest viscosity possible without any settling of the cement slurry and still obtain water loss control.

For these applications, a lower viscosity welan gum can be prepared which retains fluid loss control. Lower viscosity welan gum can be prepared by several methods. One process involves the use of hydrogen peroxide in a formulation similar to Fenton's Reagent. The formulation contains 0.15–0.25% $H_2O_2$, 0.05% $FeSO_4$ and 0.10% EDTA ethylenedinitrilo tetraacetic acid tetrasodium salt. Using this formulation a 5% welan gum solution can be degraded from greater than 10,000 cP to as low as 100 cP, as measured on a Brookfield LVT viscometer at 60 RPM. Both the degradation and the degradation rate are proportional to peroxide concentration and temperature. Therefore, one can make welan gum having a range of viscosities and yet exhibit good fluid loss control.

This low viscosity welan gum can be prepared from fermentation broth or from dry powder. To minimize peroxide use, the gum may first be purified as by the use of a proteolytic enzyme prior to further treatment.

The fermentation broth is then heated to 140° F. (60° C.) and ferrous sulfate plus tetrasodium EDTA added as a solution. Hydrogen peroxide is then added over a period of 1–3 hours. The viscosity drop is monitored to only 80 cP, spindle 2, 60 rpm, at which point the fermentation broth is cooled to 80° F. (26.6° C.) and neutralized using dilute potassium hydroxide. The low viscosity welan gum is then precipitated with isopropanol, dried, and milled.

If dry powder is used ferrous sulfate plus $Na_4EDTA$ is dissolved in water followed by the welan gum and hydrogen peroxide. The solution is heated for 1–2 hours at 75° C., and the viscosity monitored. The solution is cooled, precipitated with isopropanol, dried, and milled.

Following degradation, the low viscosity polysaccharide is recovered from solution by precipitation with 2–4 volume of isopropanol, followed by drying and milling.

Low viscosity welan gum of this invention is useful in a variety of industrial and agricultural applications. Such uses include textile printing and dyeing, especially in foamed dye or ink formulations; paper printing, especially foamed ink formulations; petroleum operations, including oil well fluids for drilling and workover operations; lithography, as in lithographic fountain solutions; detergents; microencapsulation; coatings; inks; ceramics; binders; protective colloids; agricultural foam markers; fire fighting foams, including fluoro and nonfluoro based proteins and non protein agents, and hydraulic cement compositions.

Those skilled in the art recognize that other chemical treatments, for example acid or caustic degradation, exist that would also yield lower viscosity welan gum.

There are also applications in which welan gum exhibiting high viscosities (i.e., welan gum having a 0.25% viscosity in the range of 1500–4500 cP as measured on a Brookfield LVT viscometer, spindle #2, at 3 rpm) is desirable. Such a gum can be prepared by treating a welan gum solution with enzyme. Generally, after the welan gum fermentation is complete, the pH is adjusted to 9.0 using KOH. The beer is then heated to 49-52° C., an alcalase enzyme is added at a concentration of 500-1500 ppm, and the beer mixed and aerated for 6 hours. The resulting product is then cooled to 29°-32° C. and precipitated with isopropyl alcohol.

Welan gum has distinct advantages in cement compositions.

1. It reduces the fluid loss of cement compositions, even at high temperatures.
2. The fluid loss control of welan gum is directly proportional to polymer concentration, unlike the cellulosics which increase logarithmically.
3. It greatly increases the suspension properties of cement compositions.
4. Welan gum increases the workability of cement and concrete compositions, i.e., it improves the ability of cement slurries to be easily placed in crowded areas such as around re-inforcing bars without aggregate settling.
5. The suspension properties of welan gum can also help entrain air into cement compositions such as mortar and gunite.
6. It does not retard the set of cement compositions, compared to cellulosic additives.
7. Much lower concentrations of welan gum can be used to achieve effects comparable to other additives.
8. Welan gum does not require the use of a dispersant, as do other additives, when used as a water loss control agent.

Table I is a list of representative cement additives which are useable in compositions of this invention. As the specific formulation of these additives are proprietary, they are shown in the table by the trademarks of five different vendors thereof. This listing is not a suggestion that the products included can be directly substituted one for the other.

TABLE I

Oil Field Cement Additives

Accelerators

Calcium chloride, sodium silicate (Diacel A), sodium chloride (salt), ammonium chloride (NH4Cl), or combinations or solutions of these salts are used by cementing companies. Some trade names of these products are:

| Western Co. | Dresser Titan | Halliburton | Dowell-Schlumberger | B J |
|---|---|---|---|---|
| WA-4 | MCA-L | HA-5 | S-1 | A-7 |
|  | MA-2 |  | D-77L | A-7L |
|  | Diacel A |  | S-57 | A-5 |
|  |  |  | D-44 | A-2 |

Retarders

Calcium or sodium lignosulfonates or other lignin derivatives, borax compounds, CM HEC*, sodium or calcium gluconates, and sugars are used in combinations or solutions by cementing companies and are marketed as:

| Dress Titan | Halliburton | D-S | B J Titan | Western Co. |
|---|---|---|---|---|
| MLR-1 | HR-7 | D-13 | Kembrank | WR-1 |
| MLR-3 | HR-4 | D-28 | R-5 | WR-2 |
| MHR-8 | HR-12 | D-93 | R-11 | WR-6 |
| MHR-9 | HR-15 | D-8 | M-6R.9 | WR-7 |
| MFLR-7 | Diacel LWL | D-99 | R-6 | Diacel LWL |
| MHR-600 | HR-20 | D-81 | R-17 |  |
| MHR-600 | HR-6L | D-109 | R-12L | WR-L1 |
| MLR-L | HR-13L | D-120 | R-14L |  |
| MHR-L | HR-5 | 17-133 |  |  |
|  | HR-8 | D-800 |  |  |

*Carboxymethylhydroxyethylcellulose

Fluid Loss Reducers

Bentonite, high, medium and low viscosity HEC, polyethylene imines and amines, long chain alcohols, CM HEC, polyvinyl pyrrolidones, and fine inorganic solids (such as talc) are used in fluid loss reducers. Cementing companies market these chemicals or combinations of these chemicals in dry mixes or solutions as:

| Dress Titan | Halliburton | D-S | B J Titan | Western Co. |
|---|---|---|---|---|
| MFL-4 | Halad 9 | D-60 | D-19 | CF-1 |
| MRL-5 | Halad 14 | D-59 | D-22 | CF-2 |
| MFLR-7 | Diacel LWL | D-73L | R-6 | Diacel LWL |
| MRL-L | CRF-2 | D-108 | FL-10 |  |
| MXP-56 | LA-2 | D-108L | FL-19 |  |
|  | Halad 4 | D-127 |  |  |
|  | Halad 22A | D-603 |  |  |
|  |  | D-131 |  |  |

Dispersants

Sodiums citrates, sodium naphthalene sulfonates, sodium melamine sulfonates, lignin and lignin derivatives are used by cementing companies to reduce viscosities of cement slurries and to aid in fluid loss control by dispersing the particles in the slurry. They are used alone or in combinations and are marketed as:

| Dress Titan | Halliburton | Dowell-Schlumberger | B J Titan | Western Co. |
|---|---|---|---|---|
| MCD-3 | CFR-2 | D-45 | CD-31 | TF-4 |
| MCD-4 | CFR-1 | D-65 | CD-31L | TF-5 |
| MCD-L |  | D-80L |  |  |
|  |  | D-121 |  |  |
|  |  | D-604 |  |  |

Extenders and Loss Circulation Materials

Pozzalons, asphalts, gilsonites, bentonite, diatomaceous earth, and various materials are used to plug passages where loss of whole cement occurs.

Antifoam Agents

Long chain alcohols such as octanols, stearates and their salts are often marketed as:

| B J Titan | Halliburton | D-Schlumberger | B J Titan | Western Co. |
|---|---|---|---|---|
| MFR-5 | NR-P | D-46 | FP-6 | AF-8 |
| MRP-L | D-AIR 2 | D-47 L | FP-216 | AF-L |
|  |  | M-45 |  |  |

Weighting Materials

Barite, hematite, and illmenite are the primary agents use to increase the density of cement slurries.

The cement compositions of this invention can be prepared by adding welan gum to the rest of the compositions as a dry powder, or, preferably, as an aqueous suspension at the time of adding any other liquid additives or the water for pasting if no other additives are used.

The invention is further defined by reference to the following preparations and examples, which are intended to be illustrative and not limiting.

EXAMPLE 1

Compatibility of Welan Gum With Cement

The compatibility of welan gum with cement was compared to that of xanthan gum. Using two different methods of adding the gums and also using a retarding agent, in all cases xanthan gum gelled the cement slurry whereas welan gum did not.

For the following data, API type G cement was tested at 100 lb cement/5 gallon of slurry. The xanthan gum used was KELZAN*XCD (trademark of Merck & Co., Inc.).

TABLE 1-1

VISOCOSITY* OF BIOPOLYMERS IN CEMENT SLURRY

|  | WELAN | | XCD | | |
|---|---|---|---|---|---|
|  | 0.5 lb/bbl | 1 lb/bbl | 0.5 lb/bbl | 1 lb/bbl | CONTROL (No Gum) |
| Gum w/o Cement | 120 | 370 | 120 | 360 | — |
| Gum w/ Cement | 1700 | 4000 | Gelled | Gelled | 1100 |

*Fann 35, 3 rpm Viscosity (cP)
lb/bbl = pounds per 42 gallon barrel of slurry

The data of Table 1-1 were obtained by adding dry cement to gum solutions. The results show that welan thickened the slurry whereas xanthan gum produced a lumpy gelled mixture.

TABLE 1-2

VISOCOSITY* OF CEMENT SLURRIES FOLLOWING GUM POWDER ADDITION

|  | WELAN | | XCD | | |
|---|---|---|---|---|---|
|  | 0.5 lb/bbl | 1 lb/bbl | 0.5 lb/bbl | 1 lb/bbl | CONTROL (No Gum) |
| Gum w/ Cement | 3100 | 6200 | Gelled | Gelled | 2100 |

*Fann 35, 3 rpm viscosity (cP)

For Table 1-2, the gums were added as powders to the cement slurries. Viscosity increased with increasing welan gum concentration. The product was a homogenous, smooth, and soft for about 20 minutes, after which it felt solid to the touch. The xanthan gum slurry set to a solid in about 1 minute and had a lumpy, gelled appearance.

TABLE 1-3

VISCOSITY* OF CEMENT SLURRIES WITH CEMENT RETARDER FOLLOWING GUM POWDER ADDITION

|  | WELAN 1 lb/bbl | XCD 1 lb/bbl | CONTROL (No Gum) |
|---|---|---|---|
| Gum w/Cement | 1400 | Gelled | 200 |

*Fann 35, 3 rpm Viscosity

The slurries of Table 1-3 were retarded with calcium lignosulfate, followed by gum addition. The welan slurry remained smooth and set in about 4.5 hours. The xanthan slurry had a lumpy appearance.

EXAMPLE 2

Control of Fluid Loss

The control of fluid loss with increasing welan gum concentration was determined as follows. Portland cement type A, 46% water, 0.5 to 0.8% dispersant (Lomar PW), and 0 to 0.3% welan gum (all based on dry weight of cement) were mixed in an Osterizer blender. Fluid loss was measured at 26.6° C., 1000 psi $N_2$ with no back pressure. The later Table 3-1 shows that fluid loss decreases with increased welan gum concentration and that the use of dispersing agent is beneficial.

TABLE 2-1

FLUID LOSS DETERMINATION OF WELAN GUM

| DISPERSANT CONCENTRATION (%) | WELAN CONCENTRATION (%) | FLUID LOSS (ML/30 MIN.) |
|---|---|---|
| 0.5 | 0 | 185 |
| 0.5 | 0.05 | 137 |
| 0.5 | 0.1 | 128 |
| 0.5 | 0.2 | 118 |
| 0.5 | 0.3 | 74 |
| 0.8 | 0.3 | 33 |

The control of fluid loss at elevated temperatures was determined according to API Specification 10 "Oil Well Cement Testing". Table 2-2 shows that welan gum retains better fluid loss control at 127° C. than does HEC.

TABLE 2-2

HIGH TEMPERATURE FLUID LOSS DETERMINATION

|  | Fluid Loss at 127° C. (ml./30 minute) |
|---|---|
| Base cement* | >1000 |
| Base Cement + 0.8% Low Viscosity HEC | 700 |
| Base Cement + 0.3% welan gum | 220 |

*Base Cement = Portland cement type A, 0.3% high temperature retarder, 38% water.

Welan gum controls fluid loss to such an extent that the dispersant concentration can be lowered or eliminated, as shown in the following table.

TABLE 2-3

EFFECT OF WELAN GUM WITHOUT DISPERSANT

|  | Fluid Loss at 26° C. (ml./30 minute) |
|---|---|
| Neat cement | >1000 |
| Neat Cement + 0.3% welan gum | 132 |
| Neat Cement + 0.5% dispersant | 185 |
| Neat Cement + 0.3% welan gum +0.5% dispersant | 74 |

EXAMPLE 3

Suspension Properties

A slurry containing Type H cement, 0.7% dispersant, and 46% water with and without 0.3% welan gum was poured into a two foot long by one inch I.D. PVC pipe and allowed to cure at room temperature (22° C.) overnight. The tubes were maintained in a vertical position for the duration of the curing time. The tubes were then cut into two parts twelve inches from the ends of the tubes. The cement was then removed from the pipes, volumes were determined, the samples weighed, and their densities calculated. The results in the following table show that the suspension properties of welan gum yields a more uniform slurry as the slurry cures.

TABLE 3-1

| Slurry | Density (lb./gal.) | |
|---|---|---|
| | Top Section | Bottom Section |
| Base Slurry | 11.4[1] | 18.8 |
| Base Slurry + 0.3% welan gum | 14.1[2] | 14.8 |

[1] Two inches of free water on top
[2] No free water on top

EXAMPLE 4

Preparation of Low Viscosity Welan Gum

The following reagents were used to prepare low viscosity welan gum:

| | Weight (g) |
|---|---|
| Distilled Water | 750.0 |
| Welan gum | 40.0 |
| $FeSO_4$ | 0.5 |
| EDTA"4Na | 1.2 |
| 35% $H_2O_2$ | 3.5 |

The water was heated to 60° C. then placed in a Waring blender. The other reagents were added in the order shown and the mixtures sheared for 30 minutes at 60° C. The mixture was then allowed to cool to ambient temperature and the gum precipitated with four volumes of isopropanol (IPA). The precipitate was dried overnight at 60° C., then milled through a 40 mesh screen.

The viscosities of 5% solutions of the gums on a Brookfield LVT viscometer were:

| | (cP) |
|---|---|
| Welan gum | >10,000[1] |
| Low viscosity welan gum | 110[2] |

1. Spindle #4, 60 rpm.
2. Spindle #2, 60 rpm.

EXAMPLE 5

Viscosity and Fluid Loss Control of Low Viscosity Welan Gum

Portland cement Type A slurries containing 0.75% dispersant, 46% water, and either welan gum or the low viscosity welan gum described in Example 4 were prepared and tested for viscosity and fluid loss at 22° C. Note in the following table how the low viscosity welan gum controlled fluid loss without seriously increasing the slurry viscosity.

TABLE 5-1

| Viscosity and Fluid Loss Control | | | |
|---|---|---|---|
| Polymer | Polymer Concentration % | Viscosity* (cP) | Fluid Loss (ml./30 min.) |
| Low vis. welan gum | 0.2 | 900 | 16.5 |
| " | 0.3 | 1050 | 10.5 |
| " | 0.4 | 1350 | 6.5 |
| Welan gum | 0.2 | 5350 | 31** |
| " | 0.3 | 8150 | 33 |
| " | 0.4 | 10800 | 28.5 |

*Fann 35 Viscometer, 3 RPM
**31 ml./15 min.

EXAMPLE 6

Viscosity and Fluid Loss Control of High Viscosity Welan Gum

Cement compositions containing 0.2% polymer, optionally 0.5% dispersant (Lomar D, sodium melamine sulfonate), and 38% water were tested at 80° F. (26.6° C.) for viscosity and fluid loss.

Table 6-1 shows that a high viscosity welan gum (0.25% viscosity in excess of 1500 cP, Brookfield LVT viscometer spindle #2, 3 rpm) exhibits lower fluid loss values and higher viscosities than welan gum.

Slurry viscosities are shown in Bearden Units, which are measured in accordance with the American Petroleum Institute, Specification 10, 1987.

TABLE 6-1

| Viscosity and Fluid Loss Control | | | | |
|---|---|---|---|---|
| | | Slurry Visc. (Bearden Units) | | Fluid Loss (ml./30 min.) |
| Polymer | Dispersant | Initial | Final | |
| High vis. welan gum | No | 34 | 26 | 307 |
| High vis. welan gum | Yes | 18 | 23 | 93 |
| Welan gum | Yes | 13 | 16 | 181 |

EXAMPLE 7

Following a procedure similar to that of Example 3, cement slurries (44% water) were prepared with and without welan gum and dispersant and placed in 30" columns After curing, density measurements were taken every 2". The data are presented in the following tables. Densities are ±0.5 lb/gal and no densities are provided for air or water at the top of some columns.

TABLE 7-1

| Welan Gum and Sodium Melamine Formaldehyde Sulfonate | | | | |
|---|---|---|---|---|
| | | Density (lb/gal) | | |
| Inch | Cement | Cement + 1% Sikament 86* | Cement + 1% Sikament + 0.05% Welan | Cement + 1% Sikament + 0.1% Welan |
| 30 | — | — | — | — |
| 28 | 14.5 | 11 | 16.5 | 16.5 |
| 26 | 16.5 | 12.5 | 16.5 | 16.5 |
| 24 | 16.5 | 13 | 16.5 | 16.5 |
| 22 | 16.5 | 14 | 16.5 | 16.5 |
| 20 | 16.5 | 16.5 | 16.5 | 16.5 |
| 18 | 16.5 | 17.5 | 16.5 | 16.5 |
| 16 | 16.5 | 17.5 | 16.5 | 16.5 |
| 14 | 16.5 | 18.5 | 16.5 | 16.5 |
| 12 | 16.5 | 19 | 16.5 | 16.5 |
| 10 | 16.5 | 19 | 16.5 | 16.5 |
| 8 | 16.5 | 19 | 16.5 | 16.5 |
| 6 | 16.5 | 19.5 | 16.5 | 16.5 |
| 4 | 16.5 | 19.5 | 16.5 | 16.5 |
| 2 | 16.5 | 19.5 | 16.5 | 16.5 |

*Sodium melamine formaldehyde sulfonate

TABLE 7-2

| Welan Gum And Sodium Naphthlaene Formaldehyde Sulfonate | | | |
|---|---|---|---|
| | Density (lb/gal) | | |
| Inch | Cement + 1.0% Lomar D* | Cement + 1.0% Lomar + .05% Welan | Cement + 1.0% Lomar + .1% Welan |
| 30 | — | 14.5 | 15 |
| 28 | — | 16 | 15.5 |
| 26 | 11.5 | 16 | 15.5 |
| 24 | 14 | 16 | 16 |
| 22 | 17 | 16 | 16 |
| 20 | 18 | 16 | 16 |
| 18 | 18.5 | 16 | 16 |
| 16 | 18.5 | 16 | 16 |

TABLE 7-2-continued

Welan Gum And Sodium Naphthlaene Formaldehyde Sulfonate

| | Density (lb/gal) | | |
|---|---|---|---|
| Inch | Cement + 1.0% Lomar D* | Cement + 1.0% Lomar + .05% Welan | Cement + 1.0% Lomar + .1% Welan |
| 14 | 18.5 | 16.5 | 16 |
| 12 | 18.5 | 16.5 | 16 |
| 10 | 18.5 | 16 | 16 |
| 8 | 18.5 | 16.5 | 16 |
| 6 | 18.5 | 16 | 16 |
| 4 | 19 | 16 | 16 |
| 2 | 19 | 16.5 | 16 |

*Sodium naphthalene formaldehyde sulfonate

These data show that in each case, the substantially homogenous density profile of neat cement is substantially degraded by the addition of a dispersant, leading to significant density variations over the length of the columns. The addition of welan gum restores the density profile to approximately that of neat cement.

What is claimed is:

1. A low viscosity welan gum having a 5% (wt.) aqueous solution viscosity of 100 cP as measured on a Brookfield LVT viscometer, at 25° C., spindle 2, 60 rpm.

2. A process for preparing a heteropolysaccharide of claim 1 which comprises degrading a welan gum solution by heating such at 48° to 83° C. for a sufficient amount of time in the presence of 0.05 to 0.25% ethylenedinitrilo tetraacetic acid tetrasodium salt, 0.01 to 0.1% ferrous sulfate, and 2-6% hydrogen peroxide, based on the weight of heteropolysaccharide.

* * * * *